US00PP17859P2

(12) United States Plant Patent
Fick

(10) Patent No.: US PP17,859 P2
(45) Date of Patent: Jul. 10, 2007

(54) ***STACHYS* PLANT NAMED 'NPN 001'**

(50) Latin Name: *Stachys aethiopica*
Varietal Denomination: NPN 001

(75) Inventor: Amanda Fick, George (ZA)

(73) Assignee: New Plant Nursery, George (ZA)

( * ) Notice: Subject to any disclaimer, the term of this patent is extended or adjusted under 35 U.S.C. 154(b) by 0 days.

(21) Appl. No.: 11/299,958

(22) Filed: Dec. 12, 2005

(51) Int. Cl.
*A01H 5/00* (2006.01)

(52) U.S. Cl. ..... Plt./263

(58) Field of Classification Search ..... Plt./263
See application file for complete search history.

*Primary Examiner*—Anne Marie Grunberg
*Assistant Examiner*—S. B. McCormick-Ewoldt
(74) *Attorney, Agent, or Firm*—C. A. Whealy

(57) ABSTRACT

A new and distinct cultivar of *Stachys* plant named 'NPN 001', characterized by its low spreading to trailing plant habit; freely branching habit; vigorous growth habit; relatively large leaves; and relatively large light purple-colored flowers.

1 Drawing Sheet

Botanical designation: *Stachys aethiopica.*
Cultivar denomination: 'NPN 001'.

BACKGROUND OF THE INVENTION

The present invention relates to a new and distinct cultivar of *Stachys* plant, botanically known as *Stachys aethiopica* and hereafter referred to by the name 'NPN 001'.

The new *Stachys* is a product of a planned breeding program conducted by the Inventor in George, South Africa. The objective of the program is to create new strong *Stachys* cultivars with numerous large flowers and unique flower colors.

The new *Stachys* originated from a cross-pollination made by the Inventor of two unnamed *Stachys aethiopica* selections, not patented in 2000. The cultivar NPN 001 was discovered and selected by the Inventor as a flowering plant within the progeny of the stated cross-pollination in a controlled environment in George, South Africa.

Asexual reproduction of the new *Stachys* by terminal cuttings in a controlled environment in George, South Africa since November, 2000, has shown that the unique features of this new *Stachys* are stable and are reproduced true to type in successive generations.

SUMMARY OF THE INVENTION

The new *Stachys* has not been observed under all possible environmental conditions. The phenotype may vary somewhat with variations in environment such as temperature and light intensity, without, however, any variance in genotype.

The following characteristics have been repeatedly observed and are determined to be basic characteristics of 'NPN 001' and distinguish 'NPN 001' as a new and distinct cultivar:

1. Low spreading to trailing plant habit.
2. Freely branching habit.
3. Vigorous growth habit.
4. Relatively large leaves.
5. Relatively large light purple-colored flowers.

Plants of the new *Stachys* differ primarily from plants of the parent selections in the following characteristics:

1. Plants of the new *Stachys* have larger and darker green-colored leaves than plants of the parent selections.
2. Plants of the new *Stachys* have larger flowers than plants of the parent selections.
3. Flowers of plants of the new *Stachys* are darker pink in color than flowers of plants of the parent selections.

Plants of the new *Stachys* can be compared to plants of the *Stachys* cultivar Daniella, not patented. In side-by-side comparisons conducted in southern California, plants of the new *Stachys* differed from plants of the cultivar Daniella in the following characteristics:

1. Plants of the new *Stachys* grew faster than plants of the cultivar Daniella.
2. Plants of the new *Stachys* had larger leaves than plants of the cultivar Daniella.
3. Plants of the new *Stachys* had larger flowers than plants of the cultivar Daniella.

BRIEF DESCRIPTION OF THE PHOTOGRAPHS

The accompanying colored photographs illustrate the overall appearance of the new *Stachys,* showing the colors as true as it is reasonably possible to obtain in colored reproductions of this type. Colors in the photographs may differ slightly from the color values cited in the detailed botanical description which accurately describe the colors of the new *Stachys.*

The photograph at the bottom of the sheet comprises a side perspective view of a typical plant of 'NPN 001' grown in a container.

The photograph at the top of the sheet comprises a close-up view of typical leaves and flowers of 'NPN 001'.

DETAILED BOTANICAL DESCRIPTION

The aforementioned photographs and following observations and averaged measurements describe plants grown in Bonsall, Calif., in an outdoor nursery during the summer with day temperatures ranging from 18° C. to 35° C. and night temperatures ranging from 16° C. to 21° C. After rooting, plants were grown for ten weeks in 12.5-cm containers. Color references are made to The Royal Horticultural Society Colour Chart, 1995 Edition, except where general terms of ordinary dictionary significance are used.

Botanical classification: *Stachys aethiopica* cultivar NPN 001.

Parentage:

*Female parent.*—Unnamed *Stachys aethiopica* selection, not patented.

*Male parent.*—Unnamed *Stachys aethiopica* selection, not patented.

Propagation:

*Type.*—By vegetative cuttings.

*Time to initiate roots.*—About two weeks at 20° C.

*Time to develop roots.*—About three weeks at 20° C.

*Root description.*—Fine; white in color.

*Rooting habit.*—Freely branching.

Plant description:

*General appearance.*—Low spreading to trailing plant habit. Freely branching, typically about eight primary lateral branches; numerous secondary and tertiary lateral branches. Vigorous growth habit and rapid growth rate.

*Plant height.*—About 13 cm.

*Plant diameter or spread.*—About 62 cm.

*Lateral branches.*—Appearance: Square in cross-section. Length: About 34 cm. Diameter: About 2 mm. Internode length: About 4.5 cm. Strength: Strong. Texture: Pubescent. Color: 146B.

*Foliage description.*—Arrangement: Opposite, simple. Shape: Variable, broadly elliptic and becoming closer to deltoid to somewhat cordate with development. Apex: Rounded. Base: Acute to cordate. Length: About 1.8 cm. Width: About 1.6 cm. Margin: Crenate. Texture, upper and lower surfaces: Pubescent. Venation pattern: Reticulate. Petiole length: About 5 mm. Petiole diameter: About 2 mm. Petiole texture, upper and lower surfaces: Pubescent. Color: Developing leaves, upper surface: 147A. Developing leaves, lower surface: 148A. Fully expanded leaves, upper surface: 147A. Fully expanded leaves, lower surface: 147B. Venation, upper and lower surfaces: 147B. Petiole, upper and lower surfaces: 147B.

Flowering description:

*Flower arrangement and shape.*—Relatively large single bilabiate flowers arranged in axillary verticillasters. Typically two verticillasters per node each with about three open flowers. Flowers tubular with an upright banner of two fused petals, a single petal protruding lip and two lateral petal lobes. Flowers face upright and outwardly. Flowers sessile.

*Natural flowering season.*—Continuous throughout the Spring.

*Flower longevity on the plant.*—Individual flowers last about five to seven days on the plant. Flowers not persistent.

*Flower buds.*—Length: About 7 mm. Diameter: About 3 mm. Shape: Obovate. Color: 75A.

*Inflorescence size.*—Height: About 2 cm. Diameter: About 2.8 cm.

*Flowers.*—Diameter: About 8 mm by 1.2 cm. Depth (height): About 1 cm.

*Petals.*—Arrangement: Five, fused into a tube and modified into a fused banner, two laterals and a protruding lip. Length: Banner: About 5 mm. Laterals: About 3 mm. Lip: About 9 mm. Width: Banner: About 4 mm. Laterals: About 4 mm. Lip: About 5 mm. Shape: Banner: Spatulate with notched apex. Laterals: Deltoid with acute apex. Lip: Spatulate with rounded apex. Margin, all petals: Entire. Texture, all petals, upper surface: Smooth, glabrous. Texture, all petals, lower surface: Pubescent. Color: When opening, upper and lower surfaces: 75C to 75D. Fully opened, upper surface: Banner: 75A. Laterals: 75A; towards the throat, 75C. Lip: 77C; towards the throat, 75C, with small irregular splotches of 82B. Fully opened, lower surface: Banner: 75A. Laterals: 75A. Lip: 77C. Base of fused tube: 75D.

*Sepals.*—Arrangement: Five sepals fused into a star-shaped calyx. Length: About 4 mm. Width: About 2.5 mm. Shape: Elliptic. Apex: Acute. Base: Fused. Margin: Entire. Texture, upper and lower surfaces: Pubescent. Color, upper and lower surfaces: 147A.

*Reproductive organs.*—Stamens: Quantity per flower: Four. Anther shape: Oval. Anther length: Less than 1 mm. Anther color: 71A. Pollen amount: Scarce. Pollen color: 155A. Pistils: Quantity per flower: One. Pistil length: About 8 mm. Stigma shape: Two-parted. Stigma color: 57C. Style length: About 6 mm. Style color: 155D. Ovary color: 145D.

*Seed.*—Quantity: About four per flower. Size: About 1.5 mm by 1.5 mm. Color: 200A.

Disease/pest resistance: Plants of the new Lavender have not been noted to be resistant to pathogens and pests common to Lavender.

Weather tolerance: Plants of the new Lavender have exhibited good tolerance to rain and wind and have been observed to tolerate temperatures from −2° C. to 40° C.

It is claimed:

1. A new and distinct cultivar of *Stachys* plant named 'NPN 001', as illustrated and described.

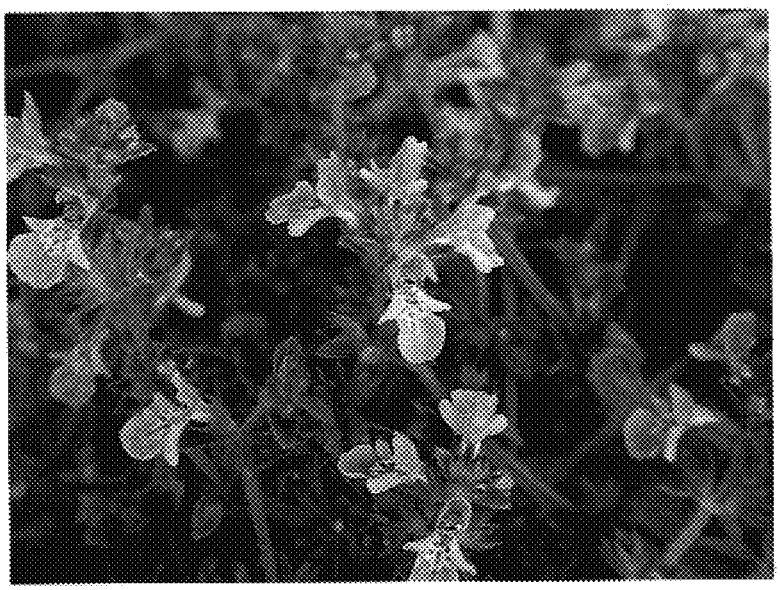
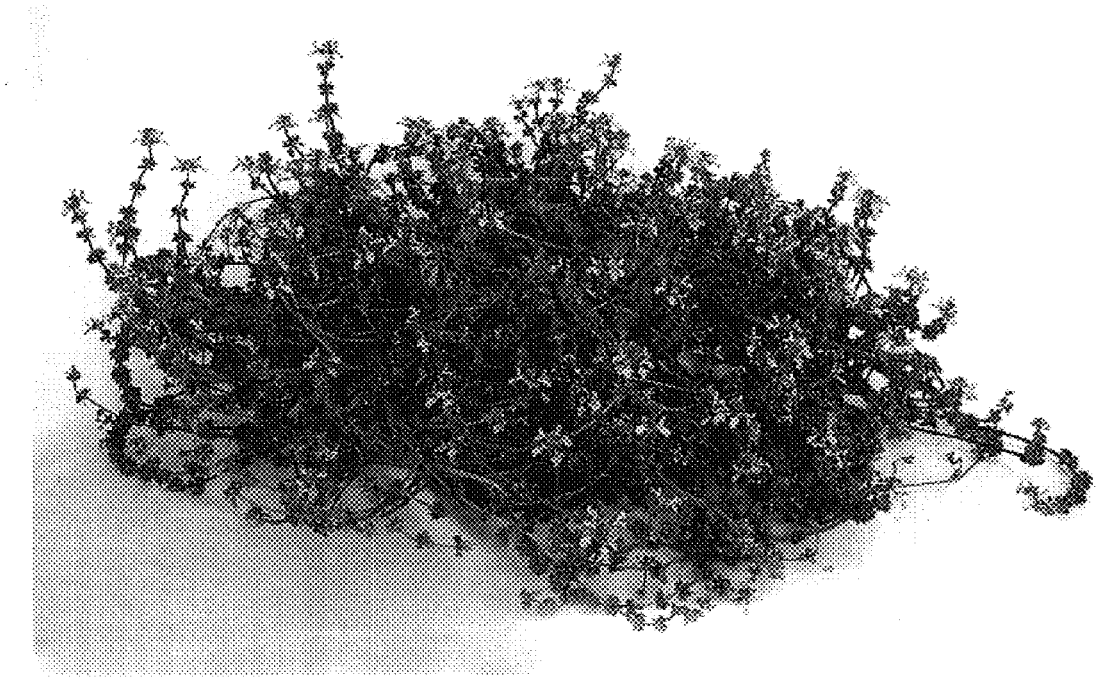

* * * * *